United States Patent [19]

Swidler et al.

[11] 4,134,722

[45] Jan. 16, 1979

[54] REACTIVE DYEING SYSTEM USING PHOSPHORUS ACID DYES WITH A CYANAMIDE COMPOUND

[75] Inventors: Ronald Swidler; William A. Sanderson, both of Palo Alto, Calif.

[73] Assignee: Burlington Industries, Inc., Greensboro, N.C.

[21] Appl. No.: 771,461

[22] Filed: Feb. 24, 1977

Related U.S. Application Data

[63] Continuation of Ser. No. 534,349, Dec. 18, 1974, abandoned, which is a continuation-in-part of Ser. No. 441,393, Feb. 11, 1974, abandoned, which is a continuation-in-part of Ser. No. 260,587, Jun. 7, 1972, abandoned.

[51] Int. Cl.$^2$ ............................................... D06P 1/38
[52] U.S. Cl. ..................................... 8/1 A; 8/1 XA; 8/3; 8/21 C; 8/39 R; 8/41 R; 8/54.2; 8/85 R; 8/89 R; 8/163
[58] Field of Search ..................... 8/1 A, 46, 3, 39 R, 8/41 R, 1 XA, 54.2, 85 R, 89 R

[56] References Cited

U.S. PATENT DOCUMENTS

| 3,363,972 | 1/1968 | Ulrich | 8/54 |
| 3,535,308 | 10/1970 | Schaefer | 260/209.5 |

FOREIGN PATENT DOCUMENTS

1230393 12/1966 Fed. Rep. of Germany.
2114998 7/1972 France.

OTHER PUBLICATIONS

O'Brien, Textile Research Journal, 1968, 38, 256–266.
van Beek and Heertjes, Melliand Textilberichte, 1963, 44, 987–993.

*Primary Examiner*—A. Lionel Clingman
*Attorney, Agent, or Firm*—Cushman, Darby & Cushman

[57] ABSTRACT

Phosphorus acid substituted chromophores are reactively linked to cellulose fibers by means of a phosphorus ester link produced in the presence of a carbodiimide such as cyanamide.

34 Claims, No Drawings

REACTIVE DYEING SYSTEM USING PHOSPHORUS ACID DYES WITH A CYANAMIDE COMPOUND

CROSS REFERENCE TO RELATED APPLICATION

This is a continuation of application Ser. No. 534,349 filed Dec. 18, 1974, which is a continuation-in-part of application Ser. No. 441,393, filed Feb. 11, 1974, which is a continuation-in-part of application Ser. No. 260,587, filed June 7, 1972, all of which are now abandoned.

BACKGROUND OF THE INVENTION

1. Field of the Invention

The present invention relates to dyeing of fibers and more particularly to reactively dyed fibers in which a chromophore is linked through a condensation residue to sites on the fiber.

2. Description of the Prior Art

Dyes are retained in fibers by physical adsorption, salt or metal-complex formation, solution, mechanical retention, or the formation of covalent chemical bonds. Physical adsorption and solution, in which the dye is partitioned between the fiber and the surrounding aqueous phase, are equilibrium reactions, and only by very careful selection of the dyes used, can good washfastness properties be achieved. Salt and metal complex formation are also equilibrium reactions and, though generally the retention of the dye is favored more than in physical adsorption, washfastness may still present a problem. The dyes that are held by mechanical retention (azoics, vats and sulfurs) are virtually insoluble in water and shown excellent fastness to washing, but have other disadvantages. They are, for example, difficult and expensive to apply; loose dye, which is not easily washed off, may be deposited on the surface, resulting in low fastness to rubbing (crockfastness), and the final shade of the dyeing does not develop until completion of the whole dyeing cycle and aftertreatments.

Chemical bonding of dye to fiber for fixation of dye was recognized as early as 1895. The reactive dye systems presently available require that the dyes contain a functional group capable of forming a covalent chemical bond with the fiber.

Fiber-reactive dyes are employed quite widely in coloring cellulosics and proteinaceous fibers. They, of course, exhibit excellent washfastness, resistance to rubbing, tinctorial powers, ease of application and leveling. The latter quality is a measure of uniformity and most important for long dye runs and color matching. The reaction of the dye with cellulosic fibers is basically an esterification or etherification reaction and is broadly represented as:

Dye—[triazine ring with N, Cl]—Cl + Cell-OH ⟶ Dye—[triazine ring with N, Cl]—O-Cell (I)

Dye—SO$_2$CH$_2$CH$_2$OH + Cell-OH ⟶ Dye—SO$_2$CH$_2$CH$_2$O-Cell (II)

The triazine reactive group imparts oil solubility characteristics to the high molecular weight dye which hinder and interfere with an aqueous solubilizing group such as —SO$_3$H. These dyes are unstable and difficult to work with. Most of the reactive dye systems are based upon chemistry where the reaction is effected in alkaline solutions. There are few present reactive dye systems which operate effectively at an acid pH. Such a system is desirable in the dyeing of mixed fabrics such as cotton blends with polyester, wool or nylon.

The American Cyanamid Company has published a booklet entitled "Cyanamide", which sets forth a considerable number of reactions of cyanamide and dicyandiamide. Page 32 of this booklet indicates that cyanamide was long known to be a dehydrating agent when warmed with anhydrous formic acid and in the esterification of lactic or salicylic acid in absolute ethanol. Note Pratorius-Seidler; G., J. prakt. Chem. [2] 21, 129-50 (1880); C. 1880, 245. A number of papers have investigated the reaction of cyanamide with carboxylic acids, and have proposed a mechanism wherein the acid is converted to the anhydride by interaction with cyanamide, with formation of urea, followed by acylation of the urea by the anhydride to produce a ureide, which at elevated temperatures interacts with the acid to produce an amide. Cyanamide and dialkylcyanamides are also useful in the synthesis of pyrophosphates. Kenner, G. W., Reese, C. B., and Todd, A. R., J. Chem. Soc. 1958, 546-51; C.A. 52, 11072 (1958) indicates that a high energy phosphorus-oxygen bond is present in the presumed intermediate O-phosphorylpseudourea.

The use of cyanamide and phosphoric acid to impart flame retardant properties to cotton and other cellulosic fabrics is well known to the art. For instance, O'Brien, "Cyanamide Based Durable Flame-Retardant Finish for Cotton", Textile Research Journal, March, 1968, pp. 256-266 indicates, at page 265, that the reaction of cyanamide and phosphoric acid with cellulose results in a cross-linking of cellulose molecules. From the properties of the resulting product, it is suggested that the cross-linked cellulose is some type of dicellulose phosphate ester.

SUMMARY OF THE INVENTION

The present invention provides a reactive dyeing system for dyeing hydroxy substituted substrates in which the reaction can be conducted in acidic to mildly alkaline solutions. The system of the invention is a reactive system in which the reactive function is not self-contained in the dye molecule. Certain dyes such as azo dyes, where the dye is formed by a simple coupling reaction, can be formed via an intermediate on the fabric which can be selectively color developed in discrete locations to form a pattern. The background areas can be treated to expose or decompose the remaining precursor areas. The dye system of the invention is further simplified in that a single group serves both as an aqueous solubilizing group and as the potentially reactive coupling site to the fiber, thus providing a more simplified synthesis and a less complex and more stable dye molecule and dyed fabric.

The dyeing system of the invention results in reactively dyed fabrics by immobilization of a dye as a cellulose phosphorus ester according to the following illustrative reaction:

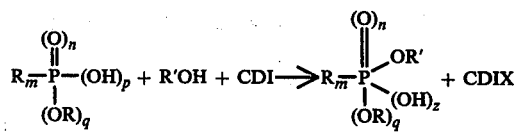

where R is a chromophore, R'OH is cellulose, CDI is a carbodiimide, CDIX is a CDI residue or by-product, m is 0, 1 or 2, n is 0 or 1, p is 1 or 2, q is 0 or 1 and z = p-1.

Thus, a chromophore (R) linked chemically to a phosphorus acid such as a phosphonic, phosphonous, phosphinic or phosphoric acid, reactively dyes cellulose (R'OH) with the aid of a carbodiimide condensing agent (CDI). Cyanamide which is a suitable carbodiimide, allows for a rapid esterification of phosphorus acids with alcohols. The by-product, CDIX, is urea. Thus, where R is a chromophore and R'OH is cellulose, a fiber reacted dye compound is formed with cellulose. This results in substantial and washfast dyeing of cotton and other cellulosic or hydroxy containing substrates. Cellulose esters of phosphonic acid dyes are found to be the most stable to heavy-duty alkaline detergents. The reaction of phosphonic acid dyes proceeds as follows:

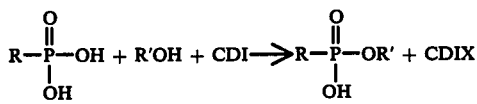

The fabric or fiber dyeing system of the invention proceeds by first forming an aqueous solution of a chromophore or precursor thereof linked chemically to a phosphorus containing acid. The solution generally contains at least 0.1% of the dye and generally no more than 10% by weight of the dye depending on the intensity of the chromophore and the shade desired. The dye concentration is generally between 0.1 and 5% by weight and the concentration of reacted dye on the fabric is believed to be in the range of 0.01 to 0.05 weight percent, although much greater concentrations of dye on the fabric can be employed, e.g., up to even 5.0 weight percent, or more.

The pH of the solution is generally about 3-4 but can be varied from about 1.5 to 9. Lower pH can be provided by addition to the impregnation bath of 1-5% of an acid which is non-volatile at the cure temperature, and does not cause undue degradation of the substrate, such as a phosphoric acid, lower alkyl phosphonic acid or chloroacetic acid. This appears to improve the efficiency of the dye immobilization since less dye is found to wash out after cure. The amount of carbodiimide is usually increased in a bath containing added acid. Higher pH baths may be utilized containing salts which are converted to the acid form during cure such as fugitive amine salts, or ammonium salts of the phosphorus acid chromophore. Higher pH baths may be necessary in certain situations which present corrosion problems, or have mixed fiber systems or fibers which would be excessively degraded at low pH.

Generally, in the bath the molar ratio of the diimide to the each phosphorus acid function is at least about 2:1. Curing is generally conducted at a temperature of at least 200° F. and generally below 400° F. Preferably, the fabric may be preliminarily dried at a temperature below 200° F. below cure. The cure time can be varied from the order of seconds to hours depending on the temperature, dye concentration and fiber being colored.

The reactive dye system of the invention is generally applicable to substrates containing available hydroxyl groups such as cellulose, particularly cotton and may be practiced on fibers, films, yarns, cords, threads, paper, fabrics, non-woven or woven, knitted; or other types including pile fabrics, velvets, knitted fabrics, corded webs or webs formed by a random webber.

The water-soluble condensation agent assists in the formation of the phosphorus ester linkage between the chromophore, R, and the cellulose substrate, R'OH. The agent is preferably a water soluble carbodiimide such as cyanamide or dicyandiamide.

The impregnating bath may also contain minor amounts of conventional additives or assistants such as anti-migrating agents, Glauber's salt, or wetting agents. Compatible thickeners may also be present.

The dyes that can be utilized in the dye immobilization process of the invention can be of diverse type and structure. The dye may be an anthraquinone, phthalocyanine, mono-azo, polyazo, benzanthrone, pyrazolone, naphthoquinone, triarylmethane or cyanine type that is modified to contain a phosphorus acid group to impart water-solubility and to provide a reactive site for attachment to the hydroxyl groups on the substrate. The dyes may contain other aqueous solubilizing groups such as sulfonate and may contain other substituents that do not interfere with aqueous solubility characteristics or the dye immobilization esterification reaction.

Many of the phosphorus acid substituted dyes utilized in the process of the invention are known materials readily available in the art, and have been used to direct dye wool and other proteinaceous fibers. Suitable dyes are disclosed in Belgium Pat. No. 570,326, British Pat. No. 455,092 and U.S. Pat. Nos. 2,596,660 and 2,799,701, the disclosures of which are incorporated herein by reference. Analogues of many sulfonated dyes can readily be synthesized in the phosphono form by substituting the phosphono analog for the sulfono containing compound during synthesis.

The process of the invention may be readily adapted so that it can be carried out in commercially available machinery used for dyeing or textile printing processes and for continuous or non-continuous variations of such processes. The fibrous or sheet material may be impregnated with the dyestuff solution and then subjected to curing by heating, for example, in a hot flue dryer, an oven or a stenter. The impregnation may be carried out for example by padding material with an aqueous solution containing the dyestuff and curing agent. The dye treatment may also be carried out by textile printing methods, for example, by locally treating the textile with solution containing the dyestuff and condensation agent and thereafter subjecting the printed material to an elevated temperature for curing. Alternatively a phosphono-substituted primary agent may be coupled to the cellulose and thereafter coupled to an azo chromophore component.

The invention will now become better understood by reference to the following detailed description when considered in conjunction with the specific examples of practice. It is to be understood that these examples are presented solely for purposes of illustration and not by way of limitation and alternative materials may readily be substituted without departing from either the spirit or scope of the invention.

DESCRIPTION OF THE PREFERRED EMBODIMENTS

The following example illustrates the synthesis of a phosphono analog of CI acid Yellow 11, a pyrazolone dye:

EXAMPLE 1

8.7 grams of 3-aminobenzenephosphonic acid and 5.3g of $Na_2CO_3$ were added to 100 ml of $H_2O$ and cooled to 15° C. 3.7g of NaNO₂ in 10 ml of H₂O were added to yield a brown solution which was slowly poured with stirring onto 21 ml of concentrated HCl containing 60g of ice. The mixture was stirred for fifteen minutes and gave a positive response to the starch - KI test.

The diazotisation method is based on Vogel, "Practical Organic Chemistry" (1951), p. 596, the disclosure of which is incorporated herein by reference, and follows the following reaction sequence:

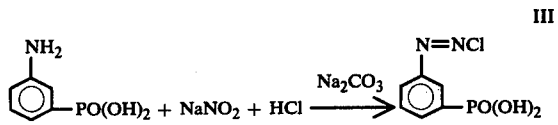

Coupling of the diazotized intermediate (III) is based on British Pat. No. 753,771. The solution containing the intermediate (III) was added to a solution containing 12.7g (1/20 mole) of 3-methyl-1-(sulfophenyl)-2-pyrazolin-5-one and 10g of sodium acetate in 100 ml of H₂O. The pH of the second solution had been adjusted from 5.3 to 7.0 with NaOH. After stirring for fifteen minutes the pH was 2.0 and there was no evidence of precipitation. On addition of isopropanol, a yellow powder was precipitated which after separation and drying in a vacuum oven yielded 13g. Coupling proceeded according to the following reaction:

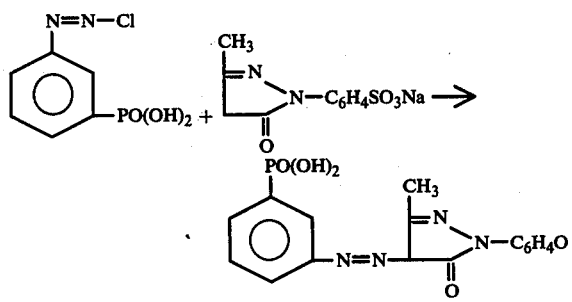

The following example illustrates the synthesis of a bis phosphono, bis-azo dye.

EXAMPLE 2

3-aminobenzenephosphonic acid was diazotized according to the procedure of Example 1 using 13 ml of concentrated HCl. 18.0g (1/20 mole) of the monosodium salt of 8-amino-1-naphthol-3,6-disulfonic acid was suspended in 50 ml of H₂O and the pH was adjusted from 2.3 to 7 with NaOH. This solution was added to the diazotate to form a dark red solution having a pH of 2.5.

Alkaline coupling was practiced according to Vogel, supra, p. 597, the disclosure of which is incorporated herein by reference.

The red solution precipitated on standing and was adjusted to pH 7 with NaOH. 40 ml of a 10% NaOH solution was then added and cooled to 5° C. A second preparation of diazotate was then added to form a blue solution having a pH of 7.4. After fifteen minutes the pH was adjusted to a pH of 2 with HCl. The dye was precipitated with isopropanol to yield 40 grams of black powder having the formula:

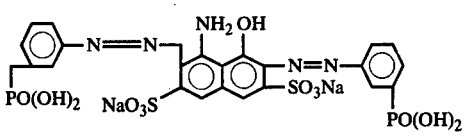

The pyrazolone yellow dye of Example 1 was used to dye cotton fabrics according to the following procedure.

EXAMPLE 3

A pad bath was prepared containing 5% of the pyrazolone yellow dye, three molar equivalents of cyanamide (1.33 weight percent) and 0.1% Triton X 100 (Rohn & Haas - octyl phenoxy polyethoxy ethanol - non-ionic wetting agent). The bath had a pH of 2.9. Samples of print cloth fabric were padded at 40 psi, and then oven dried for five minutes at 150° F. except for one fabric that was air dried at room temperature. One sample of fabric was cured for five minutes at 320° F. An oven dried fabric was cut in half for color comparison. All but one one-half of the oven dried fabrics were washed for eight minutes with heavy-duty detergent, dried and then ironed. The air-dried fabric was colorless, the oven dried fabric was colorless, whereas the cured fabric had a bright lemon yellow color with some washoff by comparison with unwashed. The colored fabrics were boiled for one hour in 3% K₂CO₃ with some color lost. The final color was a pastel yellow shade of the original bright yellow color.

Since the fabric subjected to air drying lost all color on washing, it is apparent that the dye was not substantive. It is quite unexpected that the ester linkage of the fixed dye is stable to hot detergent alkaline medium since it would be expected that the phosphorus ester moiety would hydrolyze and rupture the dye attachment.

The blue dye of Example 2 was utilized to color cotton fabric according to the following procedure:

EXAMPLE 4

A pad bath was prepared containing 5% of the blue dye plus 6 molar equivalents of cyanamide (1.73%) and 0.1% of Triton × 100. The pH of the bath was 2.6. Samples of cotton fabric were treated, dried and cured as in Example 3. After washing, the air-dried fabric was almost colorless. The oven dried fabric was a very pale blue whereas the cured fabric was a very dark navy blue. There was some slight washoff by comparison with the unwashed fabric. The warp shrinkage was −3.75% whereas the fill shrinkage was +0.75%. After the fabric was boiled for one hour in 3% K₂CO₃, the final color was a dark purple.

It was then attempted to fix the dye of Example 1 on fabric using heat without the presence of a carbodiimide.

EXAMPLE 5

A bath was prepared, containing 5% by weight of the pyrazolone yellow dye of Example 1, plus 0.1% Triton × 100. The pH of the bath was 2.9. The bath did not contain any carbodiimide or equivalent material.

Samples of cotton fabric were padded at 40 psi, dried for five minutes at 150° F. and cured for five further minutes at 320° F., washed in heavy-duty detergent and ironed. The fabrics contained only a trace of yellow color. A dye and heat step at curing temperature is not capable of fixing the dye on the fabric.

It was then attempted to fix on fabric the dye of Example 1 by means of a pad bath containing urea.

EXAMPLE 6

A bath was prepared containing 5% by weight of the pyrazolone yellow dye of Example 1, 0.1% Triton × 100 and 1.9% urea (3 molar equivalents). The pH of the bath was 2.9.

Samples of cotton fabric were treated as in Example 5 and the samples retained no more color than those of Example 5 showing that no dye immobilization occurred by this procedure.

It was then attempted to fix the dye of Example 2 on fabric using heat or urea in the absence of a carbodiimide.

EXAMPLE 7

Two baths were prepared, one containing 5% of the blue dye of Example 2 plus 0.1% Triton × 100 and the other additionally containing 2.5% urea (6 molar equivalents). The pH of the first bath was 2.65 and that of the second bath with urea was 2.70. Samples of cotton fabric were padded at 40 psi, dried for five minutes at 150° F., cured for five minutes at 320° F., washed in heavy-duty detergent and ironed. Only a trace of blue remained in the fabrics. Colors were all about the same.

The following example shows the use of polyvinyl alcohol and phosphoric acid as adjuvants to the coloring bath:

EXAMPLE 8

A pad bath was prepared containing 1% by weight of the blue dye of Example 2, 1% $H_3PO_4$, 1.6% cyanamide and 6 milliliters of 4% polyvinyl alcohol. No wetting agent was added. The pad bath was used to treat 100% cotton cloth and 50-50 cotton polyester cloth, according to the procedure of Example 3. The cloths showed good color retention and stability with very little washoff and very good resistance to boiling $K_2CO_3$. A similar bath containing 4% Cellosize in place of polyvinyl alcohol gave a similar result and also imparted some blue color to glass cloth.

The following example illustrates the use of dicyandiamide in place of cyanamide.

EXAMPLE 9

A pad bath was prepared containing 1.5% by weight of the yellow dye of Example 1 and 1% of dicyandiamide. (0.8% would be a molar ratio of 1:3.) Samples of cotton cloth were treated according to the procedure of Example 3. After washing, the dye immobilization was essentially the same as with the cyanamide treated fabrics of Example 3.

The following example illustrates preparation of the benzyl phosphonic analog of the dye of Example 1.

EXAMPLE 10 p-Aminobenzyl phosphonic acid was coupled with the sulfophenyl pyrazolone utilized in Example 1 utilizing 9.4 grams of the benzyl acid (0.1 mole) in place of 8.7 grams of the phenyl acid. The pH was finally adjusted to 3.0 with HCl and the solid precipitated with isopropanol, presumably as the monosodium salt having the structural formula:

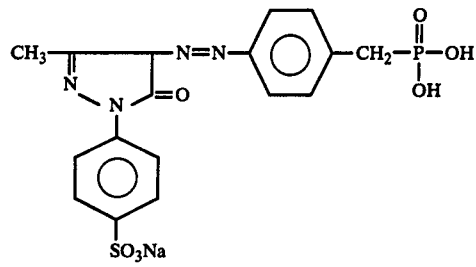

The dye exhibited similar behavior when utilized to color cotton fabric samples according to the procedure of Example 3.

The following experiment illustrates the preparation and use of the ammonium salt of the dye of Example 1 at higher pH.

EXAMPLE 11

An ammonium salt of the yellow dye of Example 1 was prepared by dissolving the dye in an aqueous $NH_4OH$ solution and evaporating the solution to dryness.

A pad bath was prepared containing 1% of the ammonium salt dye, 0.3% cyanamide and 0.25% Alipal CO 436 (nonyl phenoxy polyethoxy ethanol-sulfated, $NH_4^+$ salt). The pH of the bath was 5.8. The bath was applied to fabric and cured as in Example 3. The dye immobilization was substantially the same as in Example 3.

EXAMPLE 12

An acid pad bath was prepared containing 1% of the sodium salt of the phenyl dye of Example 1, 0.25% of Alipal and 3% of $H_3PO_4$ and 4.5% of cyanamide which represented a molar equivalent ratio of (3:1) of the cyanamide to the combined dye and acid. The pH of the pad bath was 1.8.

Samples of fabric cloth impregnated, cured and washed according to the procedure of Example 3 showed very little washoff. U.V. analysis of the cloth indicated about 75% dye fixation.

EXAMPLE 13

Methyl phosphonic acid (MPA) was substituted for the $H_3PO_4$ of Example 12 and the cyanamide content was reduced by 1.3% to adjust the MPA/cyanamide molar equivalent ratio to 1:2. The pH of the bath was 1.8. Samples of fabric, impregnated, cured and washed according to the procedure of Example 3 again demonstrated very little washoff. A sample of fabric which was air-dried before cure to minimize migration showed somewhat improved color retention.

The following experiment shows the necessity of a phosphorus acid group in the dye molecule.

EXAMPLE 14

A pyrazolone dye was prepared utilizing metanilis acid in place of the 3-aminobenzenephosphonic acid of Example 1. A bath was prepared containing 1% of the sulfonated dye, 3% $H_3PO_4$, 0.25% Alipal and 4.5% cyanamide. The pH of the bath was 1.75. Samples of fabric impregnated, cured and washed according to the procedure of Example 3 showed extreme washoff demonstrating that little or no dye was fixed.

Fixation and immobilization of dye by formation of a phosphorus acid ester linkage was further confirmed by the following experiment.

EXAMPLE 15

A solution of 5% 3-aminobenzenephosphonic acid containing 3 molar equivalents of cyanamide was utilized to impregnate cotton cloth. The cloth was cured at 320° F. for five minutes to couple the amine base to the cellulose through the phosphono-linkage.

The cellulose-coupled amine base was then subjected to diazotization with the NaNO$_2$-HCl solution of Example 1 to form a diazonium salt. A portion of the cloth was exposed to light to decompose the diazonium salt. The fabric was then immersed in a solution of the sulfophenyl pyrazolone utilized in Example 1 and dried and washed. Color was only retained in the nonexposed areas, conforming the phosphono-ester linkage as the immobilization mechanism.

EXAMPLE 16

A copper phthalocyanine substituted with phosphonic acid and sulfonic acid groups was prepared by heating an intimate mixture of triammonium 4-sulfophthalic acid (11 g), monopotassium 4-phosphonophthalate (11 g), urea (20 g), cupric chloride dihydrate (3 g), and ammonium molybdate (0.25 g) at 250° C. The product was purified by washing with hydrochloric acid and drying in a vacuum oven at 60° C.

A bath was prepared containing 1% of this product, 1% H$_3$PO$_4$, 4.4% cyanamide and 0.25% Alipal. The pH of the bath was adjusted to 2.5 with triethanolamine. Samples of fabric impregnated, cured and washed according to the procedure of Example 3 were a greenish-blue color.

The present invention provides a novel acid system for the fast dyeing of hydroxy fibers. The reactively dyed fibers exhibit good color and are stable to hot basic media. The dye system of the present invention provides a further advantage since the dye can be recovered from the bath by precipitation on a calcium substrate such as lime, CaCO$_3$ or marble and can be regenerated by acid.

The results obtained hereinabove indicate that the process of reactively dyeing textiles and other substrates has broad applicability. The process of the present invention may be broadly applied to many substrates having an active hydrogen atom according to the well-known Zerewitinoff test (J. Am. Chem. Soc., 49, 3181 (1927)). Especially preferred are substrates having alcoholic hydroxyl (non-phenolic) groups, amino groups, or thiol groups. That is, the reactive site on the substrate may have the formula —OH: —NH$_2$(amino); —NH-(amino); or —SH. Thus the process of the present invention results in the fixation of phosphorus-containing dyestuffs on rayon. The fixation is obtained with wool but the depth of shade is not as good as with rayon. Fixation of the dyestuff is also obtained with nylon, but the depth of shade is somewhat inferior to that of wool. Of the substrates having Zerewitinoff-active hydrogen atoms, those compounds having hydroxyl groups are greatly preferred, especially organic polymers having hydroxyl groups. While the substrate may be in the form of cast or other massive articles, it is greatly preferred that the substrate be a textile fabric or a textile yarn, filament or fiber.

The results obtained with cyanamide and dicyandiamide suggest that cyanamide compounds of the general formula

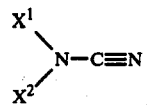

wherein $X^1$ and $X^2$ are hydrogen, lower alkyl, or together are

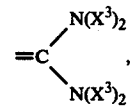

wherein each $X^3$ is independently hydrogen or lower alkyl, can be used in the process of the present invention. Thus, methylcyanamide, dimethylcyanamide, ethylcyanamide, diethylcyanamide, butylcyanamide, dibutylcyanamide, and other cyanamide compounds falling within the scope of the above formula disclosed in the aforesaid American Cyanamid Company "Cyanamide" booklet, the disclosure of which is hereby incorporated by reference, may be used in place of cyanamide or dicyandiamide Certain compounds of the above general formula may exist in tautomeric form and these tautomers are intended to be included in the general formula.

The dye, the fiber, and the cyanamide compound can be brought together in any particular order. Normally, the dye and the cyanamide compound, together with any conventional additives or assistants, will be in the form of an aqueous solution, which is padded or otherwise applied to the substrate. At least a coloring amount of the dye will be reacted onto the substrate.

As mentioned hereinabove, it is possible to form the dyestuff on the fabric essentially "in situ", by coupling a phosphono-substituted compound to the cellulose and thereafter coupling that compound to an azo chromophore component or other chromophoric group. Alternatively, the phosphorus-containing dyestuff could be applied to a textile fabric which is then subjected to an aftertreatment with the cyanamide compound. Regardless of the technique actually used, it is clear that the thrust of the present invention resides in contacting a polymeric substrate containing Zerewitinoff-active hydrogen atoms, especially alcoholic hydroxyl, amino, or thiol groups, with a cyanamide compound and with a chromophore-substituted phosphorus acid or a chromophore precursor-substituted phosphorus acid, and heating the contacted substrate to an elevated temperature to fix the chromophore or chromophore precursor to the substrate.

Mixtures of substrates, dyes, and/or cyanamide compounds may be used if desired.

The addition of phosphoric acid to the impregnating bath appears to improve the efficiency of the dye immobilization, but can have the undesirable effect of reducing the strength of the fabric by as much as about 50%. Dyes containing two phosphonate groups or other phosphorus acid groups have been found to have an efficiency of greater than 90%, when affixed to cotton or another suitable substrate by the use of cyanamide or dicyandiamide, without using any phosphoric acid in the dyebath. Since no phosphoric acid is added to the dyebath, the fabric essentially loses no strength during the dyeing process. Thus, where the strength of the textile fabric must be maintained, and high coupling efficiencies of the dyestuff achieved, the use of the dyestuffs containing two or more phosphorus acid substituents is often greatly preferred.

However, recent work has established that monophosphonate dyestuffs can produce excellent fixation on substrates, using the process of the present invention, at a pH of about 5. To achieve this pH, it is preferred to add about 0.125 to about 0.25 weight percent of phosphoric acid to the dye bath. Thus, broadly the amount of acid that can be used in the dyebath ranges from about 0.1 to about 5 weight percent.

Example 4 hereinabove relates to using a di(phosphorus acid)-substituted dyestuff. Additional examples of using such dyestuffs are set forth below.

EXAMPLE 17

H-acid (81% pure, 43.5 g, 0.1 mole) of the formula:

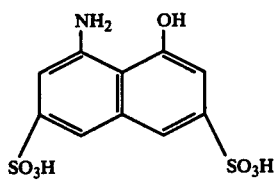

was suspended in 300 ml water and 100 g ice and the pH adjusted to 6 with sodium hydroxide solution. Sodium acetate (39 g, 0.3 mole) was added, followed by m-chlorosulfonylbenzenephosphonic acid (30 g, 0.12 mole) in portions over 10 minutes, the temperature being maintained at 10° C. and the pH at 6. The solution was stirred for three hours in an ice bath, and then sodium carbonate (25 g) was added.

To this solution was added a diazotized solution of m-aminobenzenephosphonic acid. The combined solutions were stirred for 1 hour, then concentrated hydrochloric acid (400 ml) was added and the solution filtered to yield a red dye with the structure:

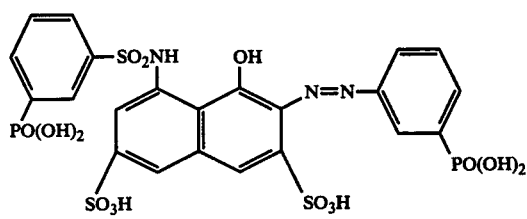

EXAMPLE 18

This and the following three examples relate to the production of orange dyes, using, as the starting compound, J acid of the formula:

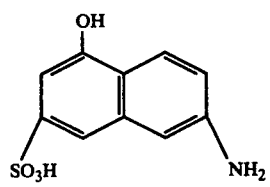

in place of the H acid. Example 17 was repeated, replacing the H acid with J acid, producing an orange dye of the formula:

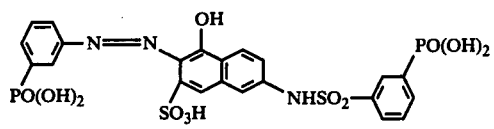

EXAMPLE 19

Example 18 was repeated, but using the N-methyl derivative of the J acid, to produce an orange dye of the formula:

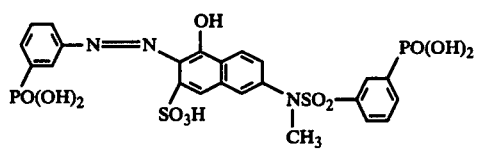

EXAMPLE 20

Example 18 was repeated, but the m-chlorosulfonylbenzenephosphonic acid was replaced by benzoylchloride, and the diazotized solution of m-aminobenzenephosphonic acid was replaced with a diazotized solution of o-amino-p-xylylenediphosphonic acid, to produce an orange dye of the formula:

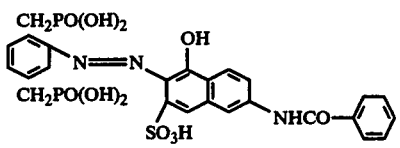

EXAMPLE 21

Example 19 was repeated, but the m-chlorosulphonylbenzenephosphonic acid was deleted, and the diazotized solution of m-aminobenzenephosphonic acid was replaced with a diazotized solution of o-amino-p-xylylenediphosphonic acid, to produce an orange dye of the formula:

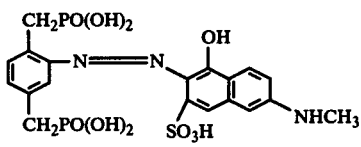

EXAMPLE 22

Following the procedure of Example 21, an orange dye was made by treating β-naphthol with diazotized o-amino-p-xylyenediphosphonic acid, and the resulting dye had the formula:

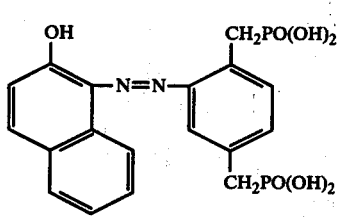

EXAMPLE 23

Example 22 was repeated, replacing the β-naphthol with F acid, of the formula:

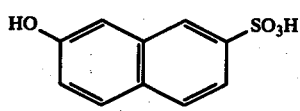

resulting in an orange dye of the formula:

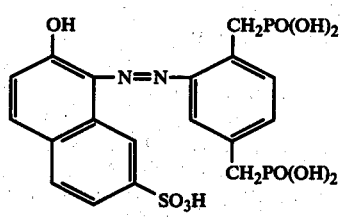

EXAMPLE 24

Bromaminic acid (89.9% pure, 132 g, 0.315 mole), p-amino benzylphosphonic acid (65 g, 0.345 mole), and cuprous chloride (12 g) were stirred in water (800 ml) and ethyl alcohol (200 ml), and sodium carbonate (160 g, 1.5 mole) added in portions. The solution was then heated to 50° C., and stirred at 45°-50° C. for 18 hours. The reaction mixture was cooled and poured carefully into concentrated hydrochloric acid (300 ml), and then filtered. The residue was recrystallized from aqueous hydrochloric acid to yield a blue dye of structure:

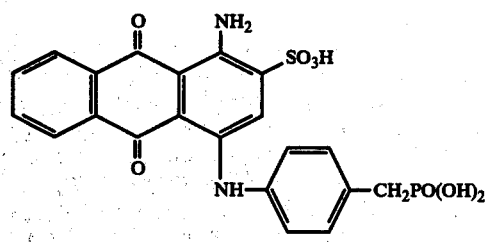

EXAMPLE 25

Example 24 was repeated, but the p-aminobenzylphosphonic acid was replaced by an equimolecular amount of o-amino-p-xylylenediphosphonic acid, to produce a blue dye of the structure:

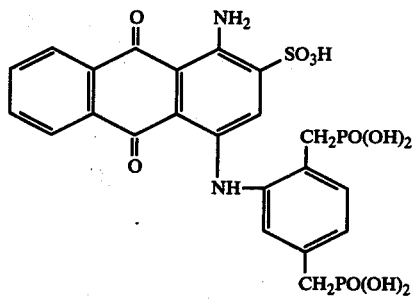

EXAMPLE 26 o-Amino-p-xylylenediphosphonic acid (28 g, 0.1 mole) was dissolved in water (150 ml) and sodium carbonate (21.2 g, 0.2 mole) added. Sodium nitrite (7.4 g, 0.107 mole) in water (40 ml) was added, and the solution was poured into a mixture of concentrated hydrochloric acid (50 ml) and ice (100 g). The solution was stirred at 5° for 20 minutes and then the excess nitrous acid destroyed with sulfamic acid. This solution was added to a solution of 3-methyl-1-(p-sulfophenyl)-2-pyrazolin-5-one (25.4 g, 0.1 mole) in water (300 ml) containing sodium carbonate (50 g), and stirred for 1 hour at 5° C. The solution was acidified with hydrochloric acid and from it was isolated the yellow dye:

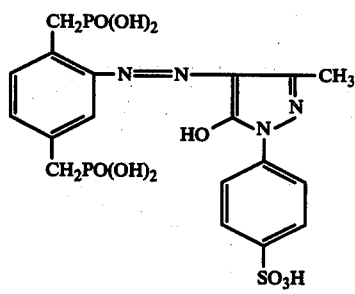

EXAMPLE 27

A pad bath was prepared containing 1% of the orange dye of Example 23, 2% of dimethylcyanamide (about 15 molar equivalents) and 0.1% Triton X100. Samples of a a multicomponent fabric containing discrete bands of wool, viscose rayon, silk, nylon, cotton, and Dacron were padded at 40 psi, oven dried for 2 minutes at 180° F. and cured for 1.5 minutes at 390° F. The fabrics were washed in detergent, rinsed and dried. Under these conditions, the wool was only slightly tinted and the Dacron unaffected. The rayon and cotton were dyed a bright orange, the nylon was dyed pink, and the silk was dyed a darker shade of orange than the cellulosic fibers.

EXAMPLE 28

An aqueous dye solution was made, with the solution containing 1% by weight of the orange dye of Example 18, 1% by weight of cyanamide, and 0.1% by weight of a surfactant (Triton X100). Rayon, nylon and wool fabrics were immersed in the dye solution, dried for five minutes at 180° F. and cured for 90 seconds at 390° F. After one home laundering the dyed samples showed significant dye fixation, with the rayon dyed the most strongly, followed, in order, by wool and nylon.

EXAMPLE 29

Separate aqueous dye solutions were prepared with each of the orange dyes of Examples 19, 20 and 23, each solution containing 1% by weight of the dye and 1% by weight of cyanamide. Separate cotton fabrics were then immersed in the respective dye solutions and then dried for five minutes at 180° F. and thereafter cured for 90 seconds at 390° F. After one home laundering all of the dyed samples showed excellent dye fixation.

EXAMPLE 30

An aqueous dye solution was made with the solution containing 1% by weight of the yellow dye of Example 26 and 1% by weight of cyanamide. Cotton fabrics were immersed in this dye solution, dried for five minutes at 180° F. and cured for 90 seconds at 390° F. After one home laundering the dyed samples were a bright yellow color and had excellent dye fixation.

EXAMPLE 31

An aqueous dye solution was made, containing 0.5% by weight of the blue dye of Example 25 and 3% by weight of dicyandiamide, this solution having pH of 2. Cotton fabrics were immersed in the dye solution, dried for five minutes at 180° F. and cured for 90 seconds at 390° F. After one home laundering the fabrics were dyed a bright blue and the dye fixation was excellent.

EXAMPLE 32

An aqueous dye solution was made containing 0.5% by weight of the blue dye of Example 25 and 1.25% by weight of cyanamide, the pH of said solution then being adjusted to a level of 3 by the addition of ammonium hydroxide. Cotton fabrics were immersed in the dye solution, dried for five minutes at 180° F. and cured for 90 seconds. After one home laundering the fabrics were dyed bright blue and the dye fixation was excellent.

EXAMPLES 33-35

In a fashion generally similar to that of Example 28 above, cotton swatches were dyed in aqueous dye solutions prepared from each of the dyes of Example 21 (orange), 22 (orange) and 24 (blue). All of the dyed swatches showed excellent dye fixation after the home laundering.

COMPARATIVE EXAMPLE A

Example 28 was repeated, except the cyanamide was omitted. After one home laundering, the dyed fabrics were only tinted a very pale orange (an indication of little if any dye fixation).

Additional classes of phosphorus-containing dyes can be readily prepared, following the procedures of Examples 17-21 and 23, but replacing the H, J and F acids with the dye intermediates disclosed in U.S. Pat. Nos: 2,847,458; 2,799,701; 2,717,906; 2,553,417; the disclosures of which are hereby incorporated by reference. Additional phosphorus-containing dyes which may be used in the practice of the present invention are disclosed in the following patents: Belgium 563,439; U.S. 2,326,047; U.S. 3,339,999; U.S. 2,183,998; U.S. 3,202,550; British 970,585; West German 1042523, the disclosures of which are hereby incorporated by reference.

Additional dyes which can be produced following the procedure of Example 21, but with different naphthylenic starting materials, are of the formulae:

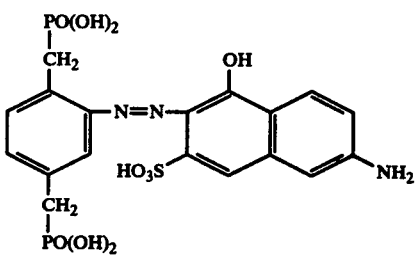

It is believed that the dyes of Examples 17, 18 and 19 are particularly novel. The results obtained with the dyes of these examples suggest that a new dye family of the class

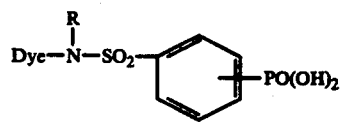

wherein R is hydrogen or lower alkyl, has been discovered. These dyes, especially those containing two or more phosphonate groups, work very well in the process of the present invention.

Of the various phosphorus-acid-substituted dyestuffs disclosed hereinabove, those dyestuffs substituted with more than one of said phosphorus acid radicals are particularly preferred, due to the excellent fixation obtained. In the latter regard, the dyes containing more than one phosphonate group have, as mentioned hereinabove, been found to be particularly preferred. The phosphonate substituents may be located at any point on the dye molecule, at generally proximate positions or at positions further removed from one another such as at the distal ends of the dye moiety.

Of the various phosphorus-acid-substituted dyestuffs disclosed hereinabove, those dyestuffs substituted with one or more phosphonate radicals are particularly preferred, due to the ease of dyeing and excellent durability obtained.

The results obtained hereinabove indicate that chromophore-substituted phosphorus acids broadly of the formula:

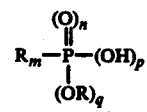

wherein each R is independently lower alkyl, aryl of 6-20 carbon atoms, aralkyl of 7-26 carbon atoms, alkaryl of 7-26 carbon atoms, or a chromophore, provided that at least one R is a chromophore, m is 0, 1 or 2, n is 0 or 1, p is 1 or 2, and q is 0 or 1, and m + p + q = 3 may be used in the process of the present invention. The chromophore-substituted phosphorus acids having hydrocarbon substituents on the oxygen atom (in addition to the chromophore) are not preferred, due to the decreased reactivity of these compounds, as well as the greater effort and expense in manufacturing same. However, it will be appreciated that such compounds may be used to replace part or all of the chromophore-substituted phosphonates or phosphates or similar compounds. Normally, only one chromophore will be attached to the phosphorus atom, either directly or indirectly (that is, it is preferred that the sum of m and q is 1, for both the formula of the preceding page and of page 7 hereinabove), and it is preferred, as indicated hereinabove, that the chromophore carry two or more phosphorus acid groups.

The present invention includes novel xylene diphosphonic acid dyestuffs of the general formula

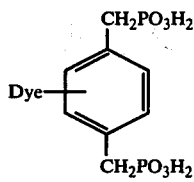

wherein Dye represents a chromophore, preferably an azoic chromophore. Such dyestuffs offer two potentially reactive sites when used in the process described herein, and thus generally result in high levels of fixation of the dyestuff on the substrate.

In addition to the preferred azoic chromophore, it will be readily appreciated by those in the art that other chromophores may be utilized. For instance, Example 25 hereinabove relates to an anthraquinone chromophore. Clearly, any of the other chromophoric groups described hereinabove, or described in the references incorporated by reference hereinabove, could be substituted for the chromophores disclosed herein in connection with the xylene diphosphonic acid dyestuffs.

EXAMPLE 36

10 g of Procion Red NX2B (CI Reactive Red 1) were dissolved in 200-250 ml of water. One gram of m-aminobenzene phosphonic acid was dissolved in 50 ml of water, using a small amount of caustic to aid solubilization. Then the phosphorus acid solution was slowly added to the dye solution with stirring. The initial pH of the dye solution was 6.5, and this pH fell to 5.5 during the addition of the phosphonic acid. The pH was adjusted to 6.8 with 50% caustic, and then the solution was warmed on a hot plate at 140° F. for 20-30 minutes.

The resulting dye solution was cooled to room temperature and 15 g of phosphoric acid and 40 g of Cyanamide 50 (50% solution of cyanamide) were added, and the resulting solution was diluted to a total volume of 500 ml. The pH of the final solution was 1.7.

The dye solution was then padded on 100% cotton fabric at a pickup of 70%. The padded fabric was dried for two minutes at 220° F. and cured for 45 seconds at 390° F. in a Benz unit. The fabric was scoured with a nonionic detergent and soda ash, and then subjected to five home launderings. The retention of color on the fabric was very good.

It is believed that the reaction between the Reactive Red 1 dyestuff and the phosphonic acid was as follows:

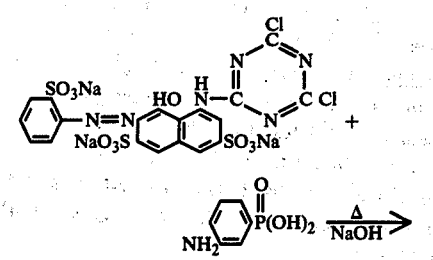

-continued

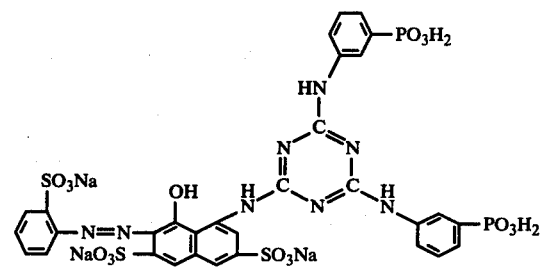

EXAMPLE 37

A reduced dye solution was prepared of a conventional monophosphate vat dye. A solution containing 5 grams per liter of the vat dye of the following formula:

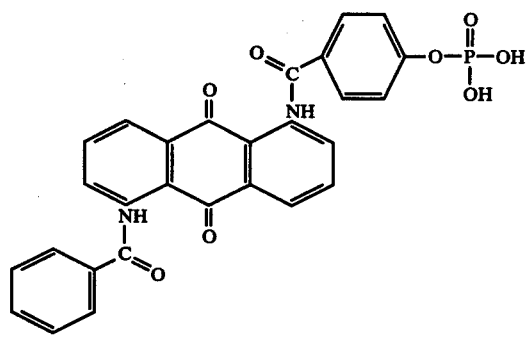

was reduced by the addition of 2 grams per liter of sodium hydrosulphite and, after the completion of the sodium hydrosulphite addition, 2 grams per liter of sodium hydroxide. The addition of the sodium hydroxide was accompanied by a color change, which would be expected for vat dyes, as denoting reduction of the dye to its soluble leuco form. Five grams per liter of a wetting agent (Igepal CO-710, obtained from GAF) was also added to the solution.

Immediately after preparation of the above reduced dye solution, a sample was padded onto 100% cotton, 3 ounce per yard sheeting, at a wet pickup of 75%. After padding, the sample was dried for 45 seconds at 220° F.

A portion of the fabric sample was rinsed in hot water (at approximately 180° F.) containing 10 grams per liter of a scouring agent (Synthrapol (R)SP obtained from ICI). A portion of the rinsed sample was then washed five times according to AATCC test method 130-1970 II. The results are reported in Table 1 hereinbelow.

EXAMPLE 38

Example 37 was repeated, up through the padding of the cotton sheeting with the reduced dye solution. The sample was then padded a second time through a 5 gram per liter solution each of acetic acid and hydrogen peroxide. After the second padding step, the sample was dried for 45 seconds at 220° F. After this oxidizing step, the sample exhibited a color change, indicating that oxidation had occurred.

Portions of the sample were rinsed and washed by the procedure of Example 37, with the results reported at Table 1 below.

EXAMPLE 39

Example 37 was repeated, through the drying step of the padded cotton sheeting. After the drying step, the sample was padded through an aqueous solution containing 80 grams per liter of cyanamide and 10 grams per liter of phosphoric acid. The sample was then dried for 90 seconds at 390° F. This curing step allowed the reaction of the dye, the cyanamide and the cellulose to occur.

This sample was treated with the rinsing and washing treatment described in Example 37. The results are reported in Table 1 below.

EXAMPLE 40

Example 38 was repeated, but after the two padding steps and the drying step, the sample was padded through the cyanamide-phosphoric acid solution described in Example 39, and then cured at 390° F. for 90 seconds.

This sample was rinsed and washed by the procedure of Example 37, and test results are reported in Table 1 hereinbelow.

TABLE 1

| Example | % Color After Rinse | % Color After 5 Washes |
|---|---|---|
| 37 Pad | 80.1 | 7.6 |
| 38 Pad ox. | 40.6 | 10.7 |
| 39 Pad/pad | 99.4 | 64.2 |
| 40 Pad/oxid/pad | 99.2 | 73.5 |

As shown in Table 1, there was some loss of color upon rinsing but the color loss was negligible for the samples of Examples 39 and 40. Washing resulted in even more dramatic differences between Examples 37 and 38, on the one hand, and 39 and 40, on the other. A definite difference in depth of shade of the samples were readily apparent. The samples of Examples 37 and 38 showed almost complete loss of color. The samples of Examples 39 and 40, however, showed much less additional color loss after washing than the samples from experiments which did not utilize the cyanamide treatement. There was no substantial increase in color yield of the sample of Example 40 over the sample of Example 39, indicating that the chemical oxidation step had little positive effect on increasing the retention of the dye in the cellulose, with the oxidation resulting in about a 9% increase in color retention.

Examples 37-40 indicate that the aftertreatment of a dyed fabric with cyanamide, accompanied by a curing step, resulting in a more stable bond formation, and therefore a higher degree of fixation and dye retention in the fiber. The normal forces involved with vat dyes, including hydrogen bonding, van derWaals and other substantive-type bonds, were insufficient to retain suitable amounts of the dye in the fiber. In distinct contrast, the reaction between the dye, the cyanamide and the cellulose created a bond which was sufficiently strong to exhibit good dye retention.

EXAMPLE 41

Example 37 was repeated, using a corresponding amount of a monophosphonate dye of the following formula:

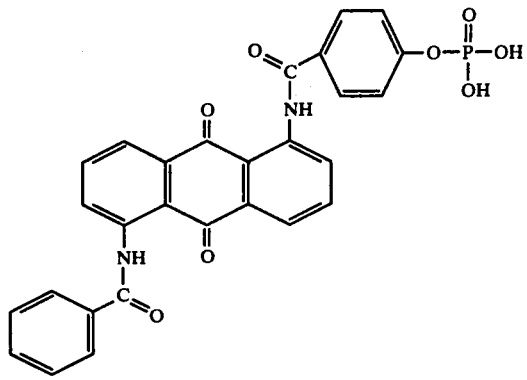

The results of evaluation of treated samples of this example are set forth in Table 2.

EXAMPLE 42

Example 38 was repeated, but using the monophosphonate dye of Example 41. The results of testing are set forth in Table 2 below.

EXAMPLE 43

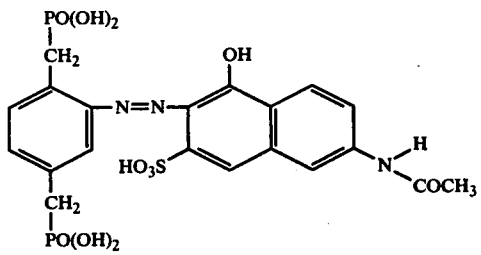

It 39 was repeated, but using the monophosphonate dye of Example 41. The results of testing are set forth in Table 2 below.

EXAMPLE 44

Example 40 was repeated, but using the monophosphonate dye of Example 41. The results of color retention testing are reported in Table 2 below.

TABLE 2

| Example | % Color After Rinse | % Color After 5 Washes |
|---|---|---|
| 41 | 38.8* | 9.6* |
| 42 | 64.5 | 13.6 |
| 43 | 89.2 | 64.0 |
| 44 | 95.2 | 71.8 |

*Average of two samples

The dyes used in Example 37 and in Example 41 were identical, except the phosphate group was replaced with the phosphonate group. The monophosphonate dye behaved in a similar manner to the monophosphate dye, with results almost identical. The results lead to basically the same conclusions as for Table 1, and also lead to the conclusion that the phosphate and phosphate dyes behave in a similar manner in their reaction with cyanamide and cotton.

EXAMPLES 45-48

Examples 37-40 were repeated, but using a monophosphate vat dye of Example 13 of U.S. Pat. No. 3,339,999, which had the following formula:

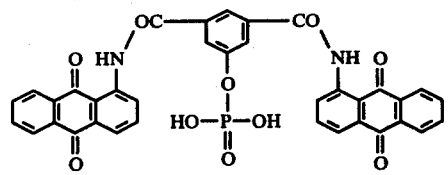

Examples 45-48 had experimental results similar to Examples 37-40.

EXAMPLES 49-52

Examples 37-40 were repeated, but using a diphosphate vat dye of Example 2 of U.S. Pat. No. 3,339,999, having the following formula:

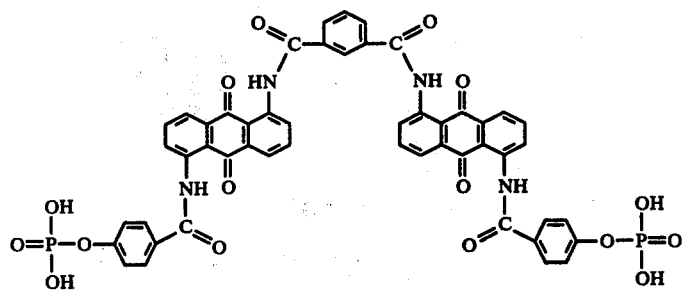

The results obtained for these examples were similar to the results obtained for examples 37-40.

EXAMPLES 53-56

Examples 37-40 were repeated, but using a diphosphate vat dye disclosed in Example 51 of U.S. Pat. No. 3,339,999, and having the following formula:

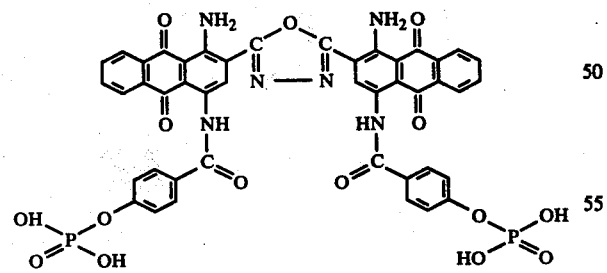

The experimental results on dyed samples of these examples were similar to the results obtained for Examples 37-40.

EXAMPLES 57-58

These examples relate to dyeings using a phosphate-containing dye which is not a vat dye, and therefore the necessity for having a reduction step is eliminated. The dyestuff used in these examples had the following structure:

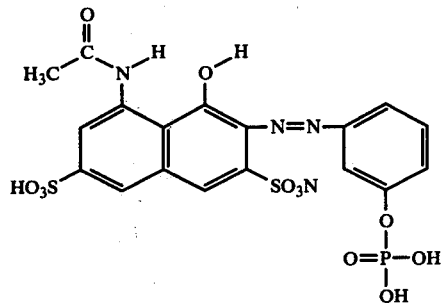

An aqueous pad dye bath solution was made, containing 0.5 weight percent of the above dye, 0.1 weight percent of wetting agent (Igepal CO-710), 1.0% of phosphoric acid, and 7% by weight of cyanamide, with all percentages based on the weight of the solution. Cotton samples were padded with the dye bath solution, using, in the case of Example 57, the dye bath solution described hereinabove, and, in the case of Example 58, the same solution but with the cyanamide and the phosphoric acid omitted.

The dyed samples of Example 57 (those containing the cyanamide and the phosphoric acid) had 73.7% color retention after rinsing, and 50.8% color retention after five washes, using the procedure of Example 37. On the other hand, Example 58, which used no cyanamide, showed practically no fixation (less than 10%).

EXAMPLES 59-60

Examples 57-58 were repeated, but using the phosphate-containing dye (which was not a vat dye) of the formula:

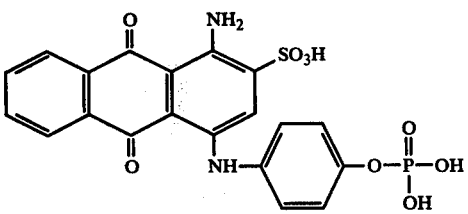

The cyanamide dye bath solution contained only 5% by weight of cyanamide, based on the weight of the solution. Example 59, which used the 5% by weight of cyanamide, and the phosphoric acid, resulted in 44.4% color retention after rinsing, and 39.3% color retention after five washes. On the other hand, Example 60, which corresponded to Example 58 in that it had no cyanamide or phosphoric acid, resulted in little or no dye fixation.

It will be appreciated from Examples 37–56 hereinabove that a practical method has been developed for the application of phosphate vat dyes to cotton and cotton-containing fabrics, with good color fixation. The prior art to date was unable to use such vat dyes commercially on cotton, because of the problem of insufficient washfastness.

EXAMPLE 61

Using the dye of Example 24, an aqueous dye bath solution was prepared, having 0.25 weight percent of the above dye, 2 weight percent of dicyandiamide, 0.1 weight percent of surfactant (Igepal CO 710) and 0.125 weight percent of phosphoric acid. A 100% cotton fabric was padded with this solution, passed through an oven at 400° F. with an exposure time of 90 seconds, and then scoured using the procedure of Example 37 and measured colorimetrically for dye retention. About 78% of the original color was retained after scouring.

EXAMPLE 62

Example 61 was repeated, except that the dye bath contained 8 weight percent, based on the weight of the bath, of a 50% aqueous solution of cyanamide in addition to the 2 weight percent of dicyandiamide. About 87% color retention was obtained.

EXAMPLE 63

Example 61 was repeated, except the dicyandiamide was eliminated from the dyebath (that is, no dicyandiamide or cyanamide was in the dyebath). The color retention after scouring was about 10%, and even more color was removed upon laundering.

EXAMPLE 64

A printing paste was prepared using 0.15 weight percent of the dye of Example 25, and 0.05 weight percent of the red dyestuff of the following formula:

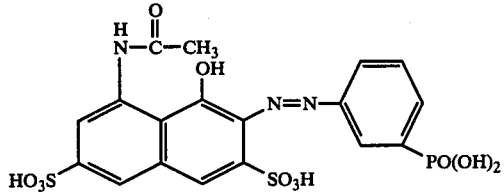

as well as 0.2 weight percent of wetting agent (Igepal CO-710)(nonylphenoxypoly(ethyleneoxy)ethanol having 10–11 ethyleneoxy units sold by GAF), 0.1 weight percent of $(NH_4)_2HPO_4$, 3.0 weight percent of dicyandiamide, 33 weight percent of 3% Keltex S (aqueous solution of sodium alginate, from Kelco Company), 33.0 weight percent of a 70% Varsol Emulsion, and the remainder water.

The resulting print paste, with pH adjusted to 8.6, was screen printed on 100% cotton fabric at an add-on of about 5 grams per square yard (about a 100% average add-on). The fabric was dried and fixed at 400° F., at an exposure time of 60 seconds, to produce a printed cotton fabric having good color retention.

EXAMPLE 65

Another printing paste was prepared, based on 0.2 weight percent of the blue dye of Example 25, 0.05 weight percent of the red dye having a structure as shown in Example 64, 0.2 weight percent of wetting agent (Igepal CO-710), 3.0 weight percent of dicyandiamide, 48 weight percent of 3% Superloid (ammonium alginate sold by Kelco Company), 15.0 weight percent of a 70% Varsol Emulsion, 2 weight percent of 50% Carbowax 4000 emulsion, and the rest water. The printing paste had a pH of about 4.2. The paste was screen printed using the procedure of Example 4, with similar results.

As mentioned hereinabove, it is, in some instances, desirable to add an acid to the dyebath in order to adjust the pH to the desired level. Phosphoric acid is a convenient, strong acid which is preferred for such pH adjustment. However, other compounds can be used, including methyl acid phosphate, ammonium phosphate, boric acid, formic acid, lactic acid, glycolic acid and sulfuric acid.

It is preferred that the dye bath contain no solvent or dye assistant, but in certain instances the use of such auxiliary chemicals may be useful. If an organic solvent is used to assist in bringing the reactants of the present invention together at the reaction temperature (that is, the dye, the cyanamide compound, and the substrate), such a solvent should contain no free alcholic-type hydroxyl group, should have a boiling point higher than that of water, and preferably should be miscible with water and the cyanamide compound. In such instances, suitable solvents might be Carbowax 350, Carbowax 750, Carbowax 2000, triethylene glycol diacetate, diethylene glycol diacetate or urea.

While a wide variety of chromophores may be used in the practice of the present invention, it is generally preferred that small dye molecules, compatible with color strength, be used. In general, long, linear dye molecules tend to position themselves along the cellulose polymer in such a manner that unreacted dye may be subjected to a slow release during subsequent washings, and not removed in adequate amounts during the production rinse.

Particularly preferred dyeing conditions for monophosphonic acid dyes include the use of about 0.2 weight percent surfactant, 0.2 weight percent phosphoric acid, no organic solvent dyeing assistant, 4.0% cyanamide and 3.0% dicyandiamide. Such a dyebath, with proper amounts of dyestuff therein, can be padded onto 100% cotton at about 75% pickup, and fixed at a temperature of about 390° F. for about 90 seconds in a Benz unit. The color endurance of the dyed fabric runs about 75–90%, with less than 5% strength loss in the fabric tear strength and warp and fill tensile strengths.

The process of the present invention for the continuous dyeing of cotton equals or exceeds other reactive dyeing systems now in use. The present process involves a pad-predry-bake-rinse-dry system which can be utilized on existing plant equipment. Most reactive dyeing systems are based upon alkaline dyeing environments, whereas the present system operates extremely well on the acid side with a pH of about 5, and thus is more compatible with the disperse dyes used in the thermosol dyeing of polyester-cotton fabrics. Dye migration problems can be controlled by normal adjustments in the padding and predrying steps in the operating plant, and such adjustments are even easier on polyester-cotton blends. The dyeings are quite consistently level. The strength loss of the cotton fabric is generally under 5%, which is about normal for reactive dyeing processing steps. The dyebaths of the present invention do not exhibit tailing (color strength loss) or ageing problems over a two-day period.

As mentioned above, the monophosphoric acid dyes used in the process of the present invention produce dyed fabrics having 70–90%, especially 75–90%, color endurance. This color endurance can be defined as the percent color retained, compared to initial unrinsed fabric, after a full rinsing and five standard AATCC machine launderings. In contrast, the color endurances for competitive reactive dyes averages about 60–70%.

Previous attempts by the art to develop an acid-side reactive dye system have been characterized by poor resistance to acid perspiration, whereas the fabrics dyed according to the present process showed little or no change in color, and little or no staining of a multifibered test fabric when tested according to AATCC Test Method 15-1975. In laundering, color loss resistance is excellent, with the results from 10–25 washes looking very favorable. The light fastness of the dyed fabrics of the present invention is at least competitive to other reactive dyes based on similar chromophores, and the same is true of similar tests, such as dry cleaning.

Another major advantage of the dye system of the present invention is that the present dyes are not subject to hydrolysis during storage, in distinct contrast to the reactive dyestuffs which are now on the market, which have a restricted shelf life. The dyes of the present invention should last indefinitely under storage conditions, and this is basically because the present dyestuffs are stable to moisture attack, as compared to the commercially available reactive dyestuffs.

In other words, the dyes of the present invention are, in their original, unreacted state, simple acid dyes which are chemically unaffected by moisture or water in any form. Thus, they will last with full efficiency for years, and this is in distinct contrast to reactive dyestuffs designed for alkaline-side dyeings.

Another major advantage of the dye systems of the present invention is the high percent fixation of the dye on the fiber which can be obtained. Normally, the alkaline-side reactive dyes have about 70% fixation or so, while fixations as high as 85% can be readily obtainable with the process of the present invention.

It is to be understood that only preferred embodiments of the invention have been described and that numerous alternatives, substitutions and modifications are all permissible without departing from the spirit or scope of the invention as defined in the following claims:

What is claimed is:

1. A method of forming a reactively dyed polymeric substrate, said method comprising
   (a) contacting a polymeric substrate containing active hydrogen atoms present in the form of alcoholic hydroxyl, amino or thiol groups, with a cyanamide compound selected from the group consisting of cyanamide, alkyl-substituted cyanamide, dicyandiamide, and alkyl-substituted dicyandiamide, wherein the alkyl groups each contain 1–6 carbon atoms, and with a coloring amount of a chromophore-substituted phosphorus acid of the formula:

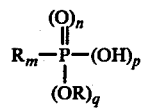

wherein R is a chromophore, m is 0, 1 or 2, n is 0 or 1, p is 1 or 2, q is 0 or 1, and m + p + q = 3, at least one of m and q being other than 0, at a pH of from about 1.5 to about 9, wherein the molar equivalent ratio of said cyanamide compound to each phosphorus acid function of said chromophore-substituted phosphorus acid is at least about 2:1, and
   (b) heating the thus contacted substrate to a temperature of at least 200° F. for a time sufficient to fix said chromophore to said substrate by condensation reaction between said active hydrogen and the phosphorus acid function of said chromophore-substituted phosphorus acid so as to join the chromophore to the substrate through the P atom.

2. Method of claim 1, wherein m is 1, n is 1, p is 2 and q is 0.

3. Method according to claim 2, wherein said chromophore is an azo chromophore.

4. Method according to claim 2, wherein said chromophore is an anthraquinone chromophore.

5. Method according to claim 2, wherein said chromophore includes an aromatic ring and is substituted with two phosphonate radicals.

6. Method according to claim 5, wherein said substrate is contacted with said cyanamide compound and said chromophore-substituted phosphonic acid in the absence of phosphoric acid.

7. Method according to claim 5, wherein the phosphonate groups are on the same aromatic ring as the chromophore.

8. Method according to claim 1, wherein said substrate is a textile substrate.

9. Method according to claim 8, wherein said textile substrate is an organic polymer containing hydroxyl groups.

10. Method according to claim 9, wherein said polymer is a cellulosic polymer.

11. Method according to claim 1, wherein said cyanamide compound is cyanamide.

12. Method according to claim 1, wherein said cyanamide compound is dicyandiamide.

13. A method of forming a reactively dyed cellulose textile substrate comprising the steps of:
   (a) contacting a cellulose textile substrate of the formula R$^1$OH, where R$^1$ is the chain of the cellulose polymer and OH is any hydroxyl group on the chain, in the presence of a cyanamide compound selected from the group consisting of cyanamide and dicyandiamide and at a pH of from about 1.5 to about 9, with a chromophore-substituted phosphorus acid of the formula:

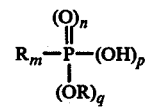

where R is the chromophore linked chemically to the P atom, m is 0, 1 or 2, n is 0 or 1, p is 1 or 2, and q is 0 or 1, at least one of m and q being other than 0, the molar equivalent ratio of cyanamide compound to each phosphorus acid function of said chromophore-substituted acid being at least about 2:1; and
   (b) heating the thus contacted substrate to a temperature of at least 200° F. for a time sufficient to react said acid with said hydroxyl to form a dyed substrate having a phosphorus ester linkage between said chromophore and chain and having the formula:

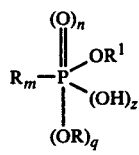

where z is p-1.

14. A method according to claim 13, in which said substrate is in fibrous form.

15. A method according to claim 13, in which the substrate is contacted by impregnating the material with an aqueous solution containing at least 0.1% by weight of a water-soluble chromophore substituted phosphorus acid.

16. A method according to claim 15, in which the acid is present in the solution in an amount from 0.1% to 5% by weight and is selected from chromophore-substituted phosphonic, phosphinic, phosphonous and phosphoric acid.

17. A method according to claim 13, in which the acid is a phosphonic acid of the formula:

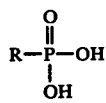

and the dyed substrate is a material of the formula:

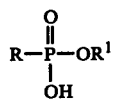

wherein R is a chromophore as defined in claim 13.

18. A method according to claim 17, in which the pH of the solution is adjusted to below about 3 by adding up to 5% by weight of an acid to the solution.

19. A method according to claim 13, in which the pH of the solution is above about 2 and the chromophore-substituted acid is in the form of a fugitive amine or ammonium salt thereof.

20. A method according to claim 13, in which the chromophore is selected from anthraquinone, phthalocyanine, azo, benzanthrone, naphthoquinone, triarylmethane and cyanine chromophores.

21. A reactively dyed hydroxy-substituted cellulose textile substrate of the formula:

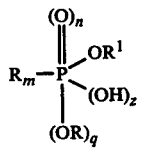

where R is a chromophore group linked chemically to the P atom, $R^1$ is the chain of the cellulose polymer, m is 0, 1 or 2, n is 0 or 1, q is 0 or 1 and z is 0 or 1, at least one of m and q being other than 0.

22. A dyed substrate according to claim 21 in which m is 1, n is 1, z is 1 and q is 0 and the chromophore is selected from the group consisting of anthraquinone, phthalocyanine, azo, benzanthrone, naphthoquinone, triarylmethane and cyanine chromophores.

23. A composition for reactively dyeing hydroxysubstituted cellulose textile substrates comprising an aqueous solution having a pH of from about 1.5 to about 9 and containing at least 0.1% by weight of a substance selected from chromophore substituted phosphorus acids and amine or ammonium salts thereof and a water soluble cyanamide compound selected from the group consisting of cyanamide and dicyandiamide in which the molar equivalent of cyanamide compound to acid is at least about 2:1.

24. A composition according to claim 23, in which the acid is a material of the formula:

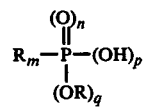

where R is a chromophore linked chemically to the P atom, m is 0, 1 or 2, n is 0 or 1, p is 1 or 2 and q is 0 or 1, at least one of m and q being other than 0.

25. A composition according to claim 24, in which the acid is a phosphonic acid of the formula:

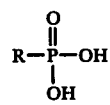

26. A composition according to claim 24, further including up to 5% by weight of an acid selected from a phosphoric acid, alkyl phosphonic acid and chloroacetic acid.

27. Composition of claim 23, wherein said chromophore substituted phosphorus acid is of the formula

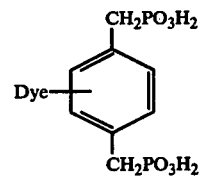

wherein Dye represents a chromophore.

28. Composition of claim 27, wherein Dye is an azoic chromophore.

29. A composition for reactively dyeing a polymeric substrate having active hydrogen atoms present in the form of alcoholic hydroxyl, amino or thiol groups which comprises a cyanamide compound selected from the group consisting of cyanamide, alkyl-substituted cyanamide, dicyandiamide, and alkyl-substituted dicyandiamide, wherein the alkyl groups each contain 1-6 carbon atoms, and a coloring amount of a chromophore substituted phosphorus acid of the formula:

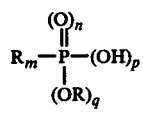

wherein R is a chromophore, m is 0, 1 or 2, n is 0 or 1, p is 1 or 2, q is 0 or 1, and m + p + q = 3, at least one of m and q being other than 0, at pH of from, about 1.5 to about 9, wherein the equivalent ratio of said cyanamide compound to each phosphorus acid function of said chromophore-substituted phosphorus acid is at least about 2:1.

30. A method of forming a reactively dyed cellulose textile substrate comprising (a) contacting a cellulose textile substrate of the formula $R^1OH$, wherein $R^1$ is the chain of the cellulose polymer and OH is any hydroxyl group on the chain, with a cyanamide compound selected from the group consisting of cyanamide, alkyl-substituted cyanamide, dicyandiamide, and alkyl-substituted dicyandiamide, wherein the alkyl groups each contain 1–6 carbon atoms, and with a coloring amount of a chromophore-substituted phosphorus acid of the formula:

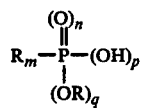

wherein R is a chromophore, m is 0, 1 or 2, n is 0 or 1, p is 1 or 2, and q is 0 or 1, and $m + p + q = 2$, at least one of m and q being other than 0, at a pH of from about 1.5 to about 9, wherein the equivalent ratio of said cyanamide compound to each phosphorus acid function of said chromophore-substituted phosphorus acid is at least about 2:1, and (b) heating the contacted substrate to a temperature of at least 200° F. for a time sufficient to react said acid with the hydroxyl group in the chain of said cellulose substrate to form a dyed substrate having a phosphorus ester linkage between said chromophore and chain and having the formula:

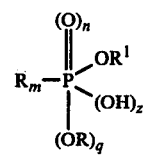

where z is p-1.

31. A method according to claim 1 wherein the chromophore-substituted phosphoric acid is a dyestuff of the formula:

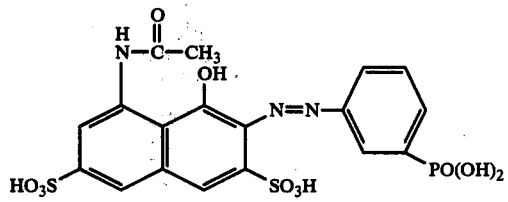

32. Method according to claim 1, wherein the contacted substrate of step (a) is dried prior to heating in step (b).

33. Method according to claim 13, wherein the contacted substrate of step (a) is dried prior to heating in step (b).

34. Method according to claim 30, wherein the contacted substrate of step (a) is dried prior to heating in step (b).

* * * * *